(12) United States Patent
Patwardhan

(10) Patent No.: US 9,192,400 B2
(45) Date of Patent: Nov. 24, 2015

(54) SURGICAL NAVIGATION

(71) Applicant: Interactive Neuroscience Center, LLC, Houston, TX (US)

(72) Inventor: Ravish V. Patwardhan, Shreveport, LA (US)

(73) Assignee: Interactive Neuroscience Center, LLC, Shreveport, LA (US)

( * ) Notice: Subject to any disclaimer, the term of this patent is extended or adjusted under 35 U.S.C. 154(b) by 199 days.

(21) Appl. No.: 13/773,181

(22) Filed: Feb. 21, 2013

(65) Prior Publication Data

US 2013/0165937 A1 Jun. 27, 2013

Related U.S. Application Data

(63) Continuation of application No. 12/525,492, filed as application No. PCT/US2008/052790 on Feb. 1, 2008, now Pat. No. 8,394,099.

(60) Provisional application No. 60/887,719, filed on Feb. 1, 2007, provisional application No. 60/942,261, filed on Jun. 6, 2007.

(51) Int. Cl.
| | |
|---|---|
| *A61B 17/16* | (2006.01) |
| *A61B 17/17* | (2006.01) |
| *A61B 17/34* | (2006.01) |
| *A61B 19/00* | (2006.01) |

(52) U.S. Cl.
CPC ......... *A61B 17/1739* (2013.01); *A61B 17/1662* (2013.01); *A61B 17/1695* (2013.01); *A61B 17/17* (2013.01); *A61B 17/1703* (2013.01); *A61B 17/3472* (2013.01); *A61B 19/52* (2013.01); *A61B 17/1637* (2013.01); *A61B 19/201* (2013.01); *A61B 19/203* (2013.01); *A61B 19/5244* (2013.01); *A61B 2017/349* (2013.01); *A61B 2019/208* (2013.01); *A61B 2019/507* (2013.01)

(58) Field of Classification Search
USPC .................................. 606/79–85, 96, 97, 172
See application file for complete search history.

(56) References Cited

U.S. PATENT DOCUMENTS

| | | | | |
|---|---|---|---|---|
| 4,186,728 | A * | 2/1980 | van Lotringen | 606/1 |
| 4,903,707 | A * | 2/1990 | Knute et al. | 600/561 |
| 4,979,949 | A * | 12/1990 | Matsen et al. | 606/53 |
| 6,432,058 | B1 * | 8/2002 | Sloth | 600/462 |
| 2005/0020909 | A1 * | 1/2005 | Moctezuma de la Barrera et al. | 600/424 |
| 2005/0251144 | A1 * | 11/2005 | Wilson et al. | 606/73 |

* cited by examiner

*Primary Examiner* — Nicholas Woodall
(74) *Attorney, Agent, or Firm* — Harness, Dickey

(57) ABSTRACT

A method of surgical navigation into the brain includes establishing a trajectory through the skull into the brain to a target, drilling a hole in the skull using a drill, and verifying the trajectory of the drilled hole during drilling using image guidance. A surgical navigation system includes a cannulated drill, a cannulated access member, and a coupling member for coupling the access member to the drill and for maintaining alignment of the cannulations in the drill and the access member. The access member is movable relative to the coupling member such that the access member can be secured to tissue while the coupling member maintains the alignment of the cannulations. A surgical kit includes a cannulated drill, a cannulated access member, a coupling member for coupling the access member to the drill, and a probe for receipt within the cannulated drill.

23 Claims, 5 Drawing Sheets

SURGICAL NAVIGATION

CROSS-REFERENCE TO RELATED APPLICATIONS

The present disclosure is a continuation application of U.S. patent application Ser. No. 12/525,492 filed on Jan. 6, 2010, which is now U.S. Pat. No. 8,394,099. This application is a National Stage Entry of International Application No. PCT/US2008/052790, filed on Feb. 1, 2008. This application claims the benefit of U.S. Provisional Application No. 60/942,261, filed on Jun. 6, 2007 and U.S. Provisional Application No. 60/887,719, filed on Feb. 1, 2007. The entire disclosures of the applications referenced above are incorporated herein by reference.

TECHNICAL FIELD

This invention relates to surgical navigation.

SUMMARY

A method of surgical navigation into the brain includes establishing a trajectory through the skull into the brain to a target, drilling a hole in the skull using a drill, and verifying the trajectory of the drilled hole during drilling using image guidance.

Embodiments of this aspect may include one or more of the following features. The image guidance is provided by a probe received by the drill. The probe is received in a lumen defined by the drill. The method includes placing an access member in the drilled hole, and verifying the trajectory of the access member during placement. The access member is placed using the drill, and the trajectory is verified using the probe received by the drill.

A surgical navigation system includes a cannulated drill, a cannulated access member, and a coupling member for coupling the access member to the drill and for maintaining alignment of the cannulations in the drill and the access member. The access member is movable relative to the coupling member such that the access member can be secured to tissue while the coupling member maintains the alignment of the cannulations.

Embodiments of this aspect may include one or more of the following features. The system includes a probe for receipt within the cannulated drill. The system includes a drill bit.

A surgical kit includes a cannulated drill, a cannulated access member, a coupling member for coupling the access member to the drill, and a probe for receipt within the cannulated drill. Embodiments of this aspect may also include a drill bit, a medical device, and/or a robot arm.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
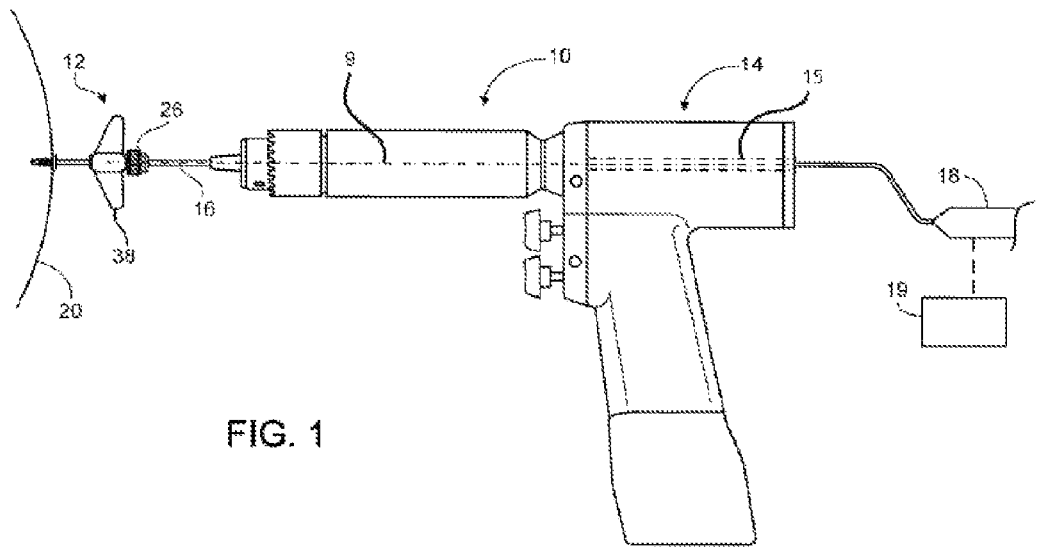
FIG. 1 is an illustration of a cannulated drill being used to place an access member in the skull under navigation guidance.

Referring to FIG. 1, an image-guided trajectory system 10 includes an access member 12 for establishing a set trajectory 9 to a target site, a cannulated drill 14, and a coupling member rod 16 that couples the access member 12 to the cannulated drill 14 during securement of the access member 12 to a patient's skull 20. Also shown in FIG. 1 is a probe 18, for example, a BrainLab Probe (available from BrainLab Cranial Navigation System) or an Integra Probe (available from Integra LifeSciences), received within the drill 14, for example, within a cannulation or lumen defined by the drill 14, such as internal lumen 15 along trajectory 9 as illustrated, and extending about half-way down the length of the drill 14. The probe 18 is coupled to an image guidance system 19, for example, a BrainLab image guidance system or an Integra image guidance system, which tracks the trajectory of the probe 18 relative to images of a patient's brain. The receipt of the probe 18 within the cannulated drill 14 during securement of the access member 12 to the skull 20 insures that the access member 12 establishes the desired trajectory to a target site.

Figure 2:
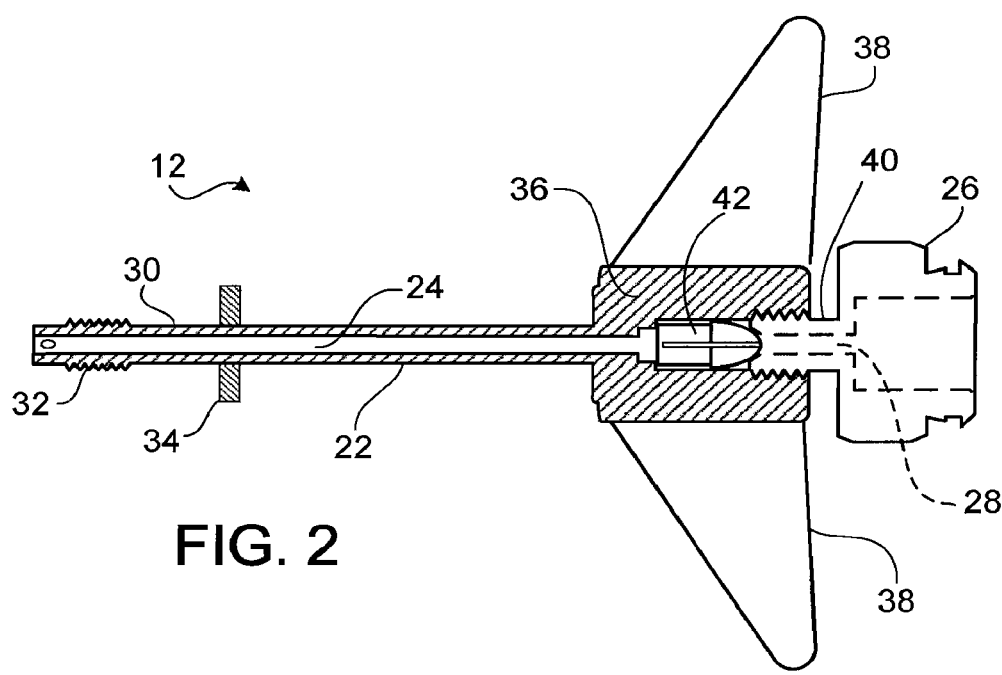
FIG. 2 is a partial cross-sectional view of the access member.

Referring to FIG. 2, the access member 12 includes a main body 22 defining an internal lumen 24, and a clamping member 26 defining an internal lumen 28 aligned with lumen 24. The main body 22 has a distal portion 30 with a threaded region 32 that engages the skull bone to secure the access member to the skull 20. Surrounding the distal portion 30 is a depth stop 34 that sets the depth to which the access member 12 is insertable into the skull. The main body 22 has a proximal portion 36 with two outwardly extending wings 38 that can be engaged by the operator's hand and turned to thread the access member 12 into the skull.

Figure 3:
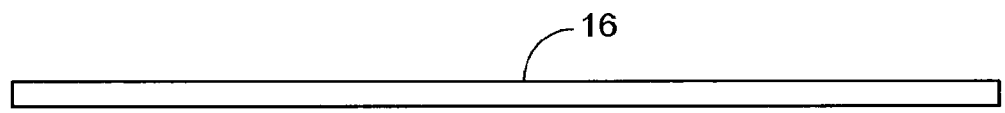
FIG. 3 is a side view of a coupling member that couples the access member to the cannulated drill.

The clamping member 26 has a threaded extension 40 that is received by the proximal portion 36 of the main body 24 and is rotatable relative to the main body 24. The clamping member 26 acts on a collet 42 located within proximal portion 36 such that rotation of the clamping member 26 causes the collet 42 to clamp onto and release the rod 16 (FIG. 3) received in the lumens 24 and 28.

Figure 4:
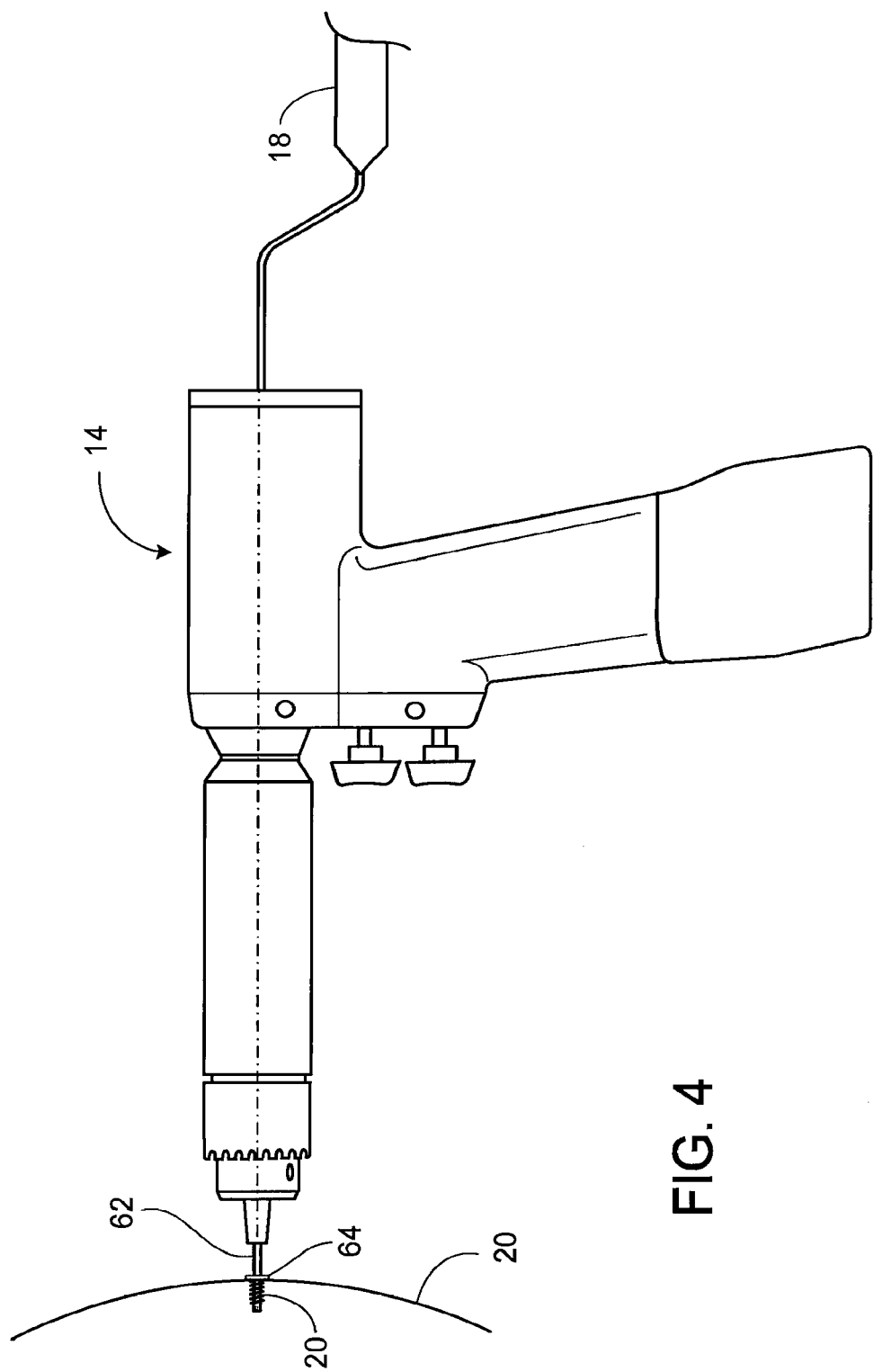
FIG. 4 shows the cannulated drill being used to drill a hole in a skull.

Referring to FIG. 4, prior to securing the access member 12 to the skull 20, the operator uses the cannulated drill 14 to drill a pilot hole 60 in the skull 20. Using a drill bit 62 and with the probe 18 received within the drill 14, the operator drills the pilot hole 60 under image guidance such that the pilot hole 60 is aligned with a desired preplanned trajectory to a target set within the brain. Surrounding the drill bit 62 is a movable depth stop 64 that sets the depth to which the drill bit 62 is insertable into the skull.

After drilling the pilot hole, the operator replaces the drill bit 62 with the rod 16 and attached access member 12, a shown in FIG. 1. The rod 16 extends about 3.5 cm into the drill 14 and about 3.5 cm into the access member 12 to axially align the drill 14 and the access member 12. The operator places the access member 12 against the entrance to the pilot hole 60 and uses the probe 18 to align the access member 12 along the desired trajectory to the target site. The operator then loosens the collet 26 such that the access member 12 can be rotated relative to the rod 16 to advance the access member 12 into the skull 20. While the rod remains attached to the drill 14 and remains within the lumens 24, 28 during rotation of the access member 12, the rod 16 need not move, that is, is not rotated, during the advancement of the access member 12. While applying a force to the wings 38 to thread the access member 12 into the skull 20, the operator verifies the alignment of the access member 12 along the trajectory using probe 18 positioned within drill 14.

Figure 5:
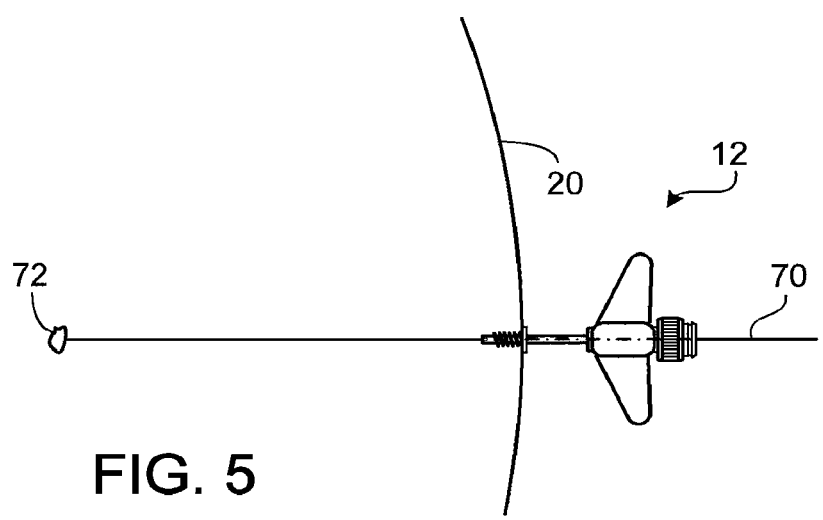
FIG. 5 shows the access member being used to position a medical device at a target site within the brain.

The operator then removes the drill 14 and rod 16 from the access member 12. Referring to FIG. 5, the access member 12 now establishes a set trajectory for introduction of various medical devices 70, e.g., ventriculostomy catheters, other directed catheters for convection therapy, epilepsy depth electrodes, thermocoagulation probes, lesioning probes, stereotactic needles, and ablative probes, to the target site 72. The operator need only control the depth of advancement of the medical device, which, in many cases, can be predetermined using navigation software.

To further increase the accuracy of the device placement through the access member 12, the drill 14 can directly hold the access member after securement of the access member to the skull 20, and the medical device can be passed through the drill and the access member to the target site.

A cannulated drill is available from Stryker (4200 Cordless Driver 2), and can be used with a step down chuck for holding the drill bit 62 and the rod 16.

Figure 6:
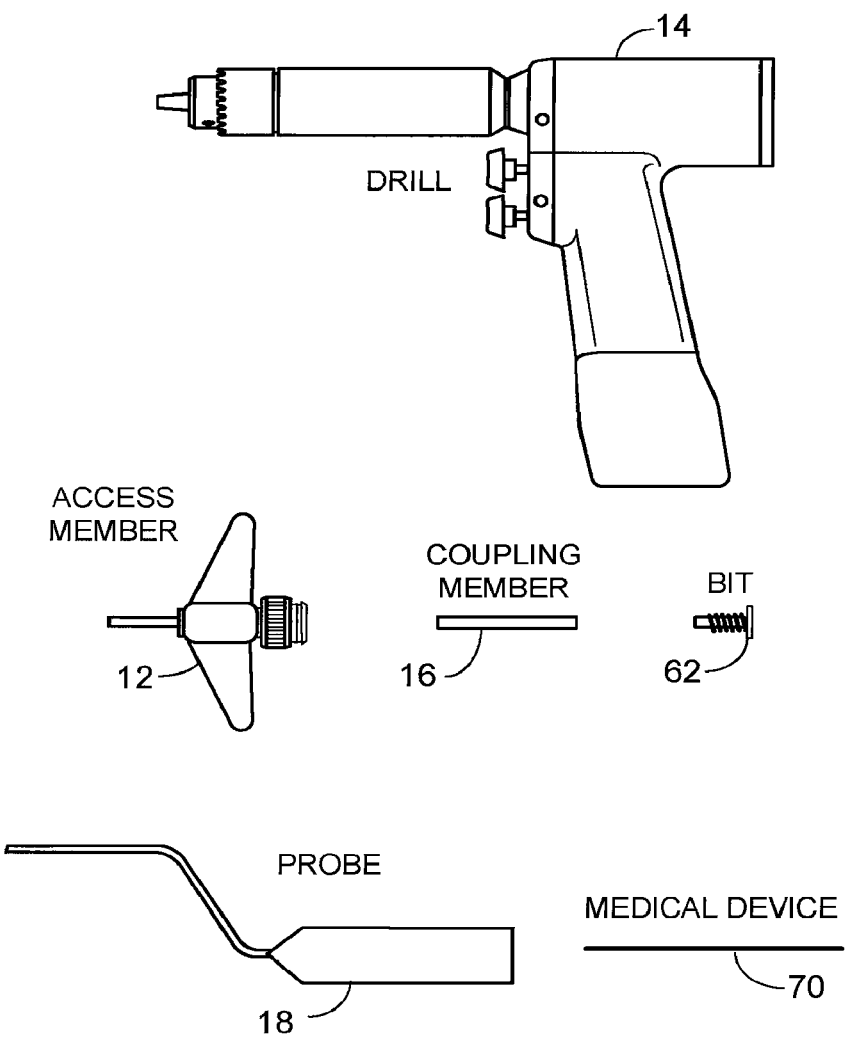
FIG. 6 illustrates an exemplary disposable kit containing components of the system.

The various components of the image-guided trajectory system 10 can be sold as kits 80 (FIG. 6), either disposable or non disposable, including one or more components of the system 10. For example, the cannulated drill 14, the access member 12, the coupling member 16, and the drill bit 62 can be packaged together for sale as a disposable kit. Alternatively, any combination of one or more of the four components can be packaged together for sale as a disposable kit, for example, just the access member 12, the coupling member 16, and the drill bit 62 can be packaged together, the access member 12 and the coupling member 16 can be packaged together, etc. The probe 18 can also be included in any of the various combinations of disposable kits described above, for example, a disposable kit can include the probe 18, drill 14, access member 12, and coupling member 16. Furthermore, one or more medical devices 70 can be included in any of the various combinations of disposable kits, including kits with the probe 18. All of the components need not be disposable. The various components can be sold as a system with the image guidance system 19.

Figure 7:
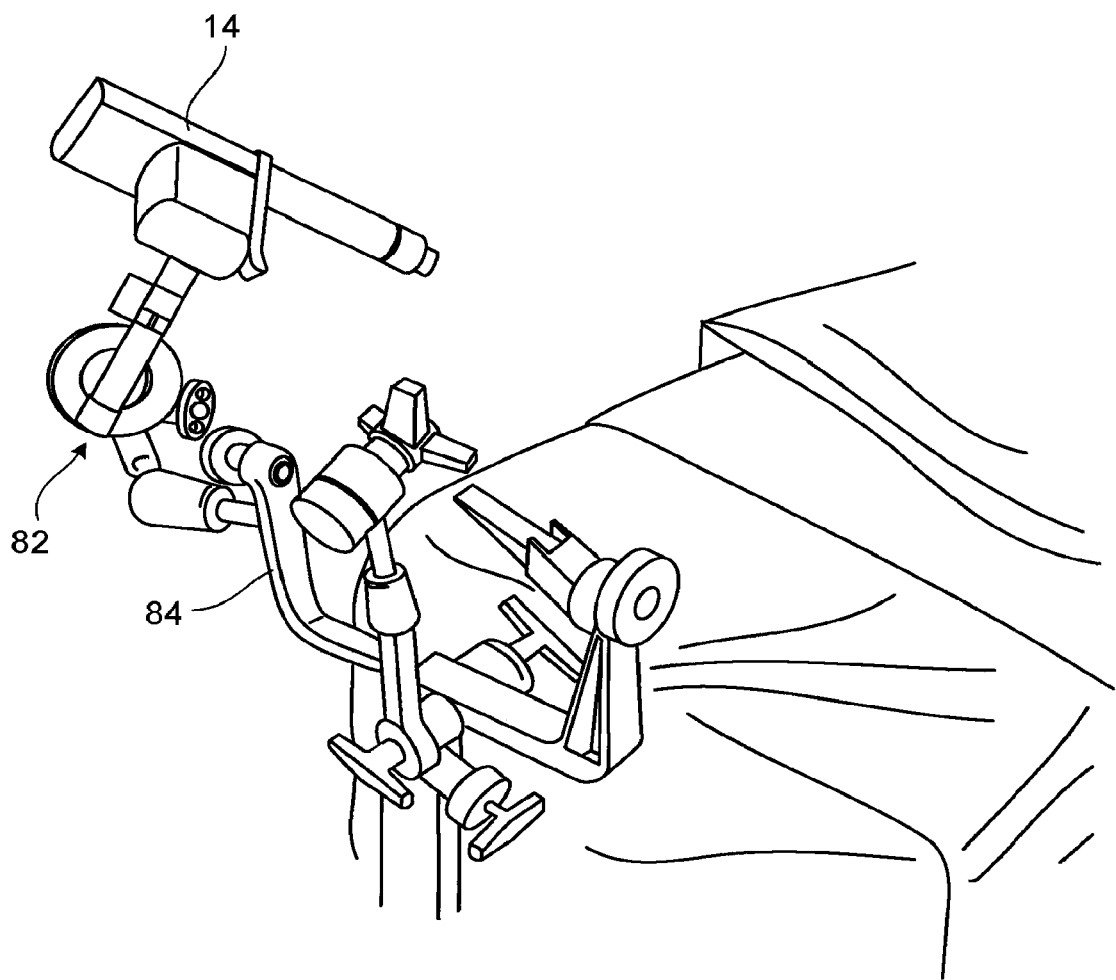
FIG. 7 illustrates a robot arm supporting the cannulated drill.

Referring to FIG. 7, the cannulated drill 14 can be supported during use by a robot arm 82, for example, a BrainLab robot arm. The robot arm 82 can be manipulated to fix the position of the cannulated drill 14 in a selected axis. The robot arm 82 is preferably supported by a device 84, for example, a Mayfield head holder, used to fixate the head. The robot arm 82 can be included in any of the kit configurations described above.

Various modifications may be made without departing from the spirit and scope of the invention. Accordingly, other embodiments are within the scope of the following claims.

The invention claimed is:

1. A system comprising:
   a cannulated drill;
   a cannulated access member comprising a first lumen;
   a clamping member comprising second lumen; and
   a rod received within the drill, the first lumen and the second lumen,
   wherein
      the clamping member couples the access member to the drill,
      the cannulated access member, while coupled to the clamping member, is movable relative to the clamping member to secure the cannulated access member to tissue of a patient while the clamping member and the rod maintain alignment of the first lumen and the second lumen,
      a proximal portion of the cannulated access member comprises a collet, and
      the collet (i) is caused to clamp down on the rod by the clamping member when the cannulated access member is tightened onto the clamping member, and (ii) releases the rod when the cannulated access member is loosened from the clamping member.

2. The system of claim 1 further comprising a medical device for receipt within the cannulated access member.

3. The system of claim 1, wherein said medical device is selected from a group consisting of a ventriculostomy catheter, convention therapy catheter, epilepsy depth electrode, thermocoagulation probe, lesioning probe, stereotactic needle and ablative probe.

4. The system of claim 1, further comprising a probe.

5. The system of claim 4, wherein said probe is adapted to be tracked by navigation software.

6. The system of claim 1, further comprising a drill bit.

7. A kit comprising:
   a cannulated drill;
   a cannulated access member comprising a first lumen;
   a clamping member for coupling the access member to the drill, wherein the clamping member comprises a second lumen;
   a rod received within the drill the first lumen and the second lumen; and
   a probe for receipt within the cannulated drill,
   wherein
      the clamping member couples the access member to the drill,
      the cannulated access member, while coupled to the clamping member, is movable relative to the clamping member to secure the cannulated access member to tissue of a patient while the clamping member and the rod maintain alignment of the first lumen and the second lumen,
      a proximal portion of the cannulated access member comprises a collet, and
      the collet (i) is caused to clamp down on the rod by the clamping member when the cannulated access member is tightened onto the clamping member, and (ii) releases the rod when the cannulated access member is loosened from the clamping member.

8. The kit of claim 7, further comprising a drill bit.

9. The kit of claim 7, further comprising a medical device.

10. The kit of claim 7, further comprising a robot arm.

11. The kit of claim 9, wherein said medical device is selected from a group consisting of a ventriculostomy catheter, convention therapy catheter, epilepsy depth electrode, thermocoagulation probe, lesioning probe, stereotactic needle and ablative probe.

12. The system of claim 1, wherein the collet is implemented within the proximal portion of the cannulated access member.

13. The system of claim 1, wherein the cannulated access member comprises wings that extend from the proximal portion and provide points of contact to grasp when turning the cannulated access member on the clamping member.

14. The system of claim 1, wherein:
   the clamping member comprises a first set of threads; and the clamping member is screwed into the cannulated access member to cause the collet to clamp down onto the medical device.

15. The system of claim 14, wherein:
the cannulated access member comprises a second set of threads; and
the cannulated access member is screwed into the tissue of the patient.

16. The system of claim 15, wherein the cannulated access member comprises a depth stop on the cannulated access member between the second set of threads and the proximal portion and limits how far the cannulated access member can be screwed into the patient.

17. The system of claim 1, further comprising a probe received by the cannulated drill, wherein a trajectory of the cannulated access member is verified via the probe during securing of the cannulated access member to the tissue of the patient.

18. The kit of claim 7, wherein the collet is implemented within the proximal portion of the cannulated access member.

19. The kit of claim 7, wherein the cannulated access member comprises wings that extend from the proximal portion and provide points of contact to grasp when turning the cannulated access member on the clamping member.

20. The kit of claim 7, wherein:
the clamping member comprises a first set of threads; and
the clamping member is screwed into the cannulated access member to cause the collet to clamp down onto the medical device.

21. The kit of claim 20, wherein:
the cannulated access member comprises a second set of threads; and
the cannulated access member is screwed into the tissue of the patient.

22. The kit of claim 21, wherein the cannulated access member comprises a depth stop on the cannulated access member between the second set of threads and the proximal portion and limits how far the cannulated access member can be screwed into the patient.

23. The kit of claim 7, further comprising:
a probe to be received by the cannulated drill; and
a drill bit to be received by the cannulated drill prior to the cannulated access member being coupled to the clamping member, wherein a trajectory of the drill bit during drilling of the drill bit into the tissue of the patient is verified via the probe,
wherein a trajectory of the cannulated access member is verified via the probe during securing of the cannulated access member to the tissue of the patient and subsequent to the drilling of the tissue of the patient and removal of the drill bit from the tissue of the patient.

* * * * *